United States Patent [19]

Kross

[11] Patent Number: 5,993,864
[45] Date of Patent: Nov. 30, 1999

[54] CHLORINE DIOXIDE CHELATE COMPOSITIONS AND METHOD OF USE

[76] Inventor: Robert D. Kross, 2506 Florin Ct., Bellmore, N.Y. 11710

[21] Appl. No.: 08/893,646

[22] Filed: Jul. 11, 1997

[51] Int. Cl.$^6$ .......................... A01N 59/00; A01N 25/22; A01N 37/44
[52] U.S. Cl. .................... 424/661; 424/665; 424/DIG. 6; 514/292; 514/334; 514/410; 514/448; 514/556; 514/561; 514/564; 514/566; 514/640; 514/667; 514/669; 514/675; 514/836; 514/970
[58] Field of Search ..................................... 424/661, 665, 424/DIG. 6; 514/970, 556, 561, 564, 566, 448, 675, 667, 669, 334, 410, 640, 292, 836; 422/37

[56] References Cited

U.S. PATENT DOCUMENTS

| | | | |
|---|---|---|---|
| 3,123,521 | 3/1964 | Wentworth et al. | 424/615 |
| 4,507,285 | 3/1985 | Kühne | 424/615 |
| 4,574,084 | 3/1986 | Berger | 424/601 |
| 4,725,437 | 2/1988 | Kühne | 424/613 |
| 4,829,129 | 5/1989 | Kelley | 424/662 |
| 5,008,096 | 4/1991 | Ringo | 423/477 |
| 5,407,656 | 4/1995 | Roozdar | 423/477 |

OTHER PUBLICATIONS

Chlorine Dioxide; W.J. Masschelein; Ann Arbor Science (1979); p. 139.

Chelating Agents; Encyclopedia of chemical Technology, vol. 5, Third Edition (1979); vol. 5; pp. 339,348,349,353.

Complex Ion Formation Between $ClO_2$ and $ClO_2-$; Inorg. Nucl. Chem Letters vol. 2., pp. 395–398, 1966. Pergamnon Press Ltd.

*Primary Examiner*—John Pak
*Attorney, Agent, or Firm*—Henry D. Coleman; R. Neil Sudol

[57] ABSTRACT

A novel chelate complex allows the formation of stable solutions of molecular chlorine dioxide. The chelate complexes are composed of the electron-deficient chlorine dioxide molecule, which can accept an electron, and a chelating agent, which can contribute its available electrons to the accepting orbital of the chlorine dioxide molecule. Both active and passive methods of releasing the chlorine dioxide from such chelates by competitive displacement with selected metal cations are presented. In this manner a stabilized solution of molecular chlorine dioxide can be stored until needed and the chlorine dioxide released at time of use for cleaning, disinfection or other uses.

8 Claims, No Drawings

CHLORINE DIOXIDE CHELATE COMPOSITIONS AND METHOD OF USE

TECHNICAL FIELD

This invention relates generally to the formation and use of novel chelate complexes of chlorine dioxide, for use in disinfecting animal tissues and inanimate surfaces, and to treat diseases and wounds. The invention also provides passive and active methods for releasing the chlorine dioxide from such chelates by competitive displacement with selected metal cations.

BACKGROUND OF THE INVENTION

Chlorine dioxide has become increasingly well known as a potent antimicrobial agent, as well as a bleaching material, in many commercial and industrial applications. As a germicide it is finding increasing use in municipal water disinfection, cooling towers and oral malodorants, where it both destroys putrefactive organisms and oxidizes the odorant. It also has been approved recently for reducing poultry pathogens during processing, surpassing the reductions which can be achieved with chlorine. Chlorine dioxide is also used as a bleaching agent in paperboard production and for textiles and flour. However, $ClO_2$ is a reactive gas which is explosive in air at levels approximating 10%, and it has a low threshold limit value (TLV) classification by OSHA of 0.1 ppm in workers' air. It cannot be compressed and stored, as can chlorine, and water solutions of chlorine dioxide rapidly degrade both through disproportionation to higher- and lower-valent chlorine species and through evaporation. As a result of these limiting properties, it is generally produced "on site," by acidification of chlorite solutions or reduction of chlorates.

Because it has superior destructive properties for bacteria, fungi and viruses, efforts have been made to capture and/or stabilize $ClO_2$ molecules in aqueous solution for subsequent use as a germicide or for more general oxidative purposes. A series of patents have issued in the last forty years, disclosing the stabilization of $ClO_2$ solutions by inclusion of various peroxides, such as sodium perborate in U.S. Pat. No. 2,701,781, and sodium carbonate peroxide in U.S. Pat. No. 3,123,521. Chlorine dioxide may form in these solutions after dilution with water, which may reduce the pH sufficiently to produce low levels of the gas at a slow rate, or by direct acidification of the solutions to hasten the process. The stabilized chlorine dioxide in these formulations has been later revealed to predominate in the reduced oxychlorine form of chlorite, with chlorine in the trivalent state, rather than as chlorine in the tetravalent state associated with $ClO_2$. The interaction of acidity with chlorites is a well recognized means of converting chlorite to chlorine dioxide. The essence of these stabilized $ClO_2$ patents is the presence of a peroxide reservoir, which acts to reduce any small levels of free $ClO_2$, that may be slowly formed, back to the more stable chlorite form. Analysis of commercially available stabilized chlorine dioxide formulations reveal, at most, only a few parts per million of free, molecular $ClO_2$.

A novel polymer composition was disclosed, in U.S. Pat. No. 4,829,129, where aqueous polymeric N-vinyl-α-pyrrolidone (PVP) solutions, ranging from 1% to 60% by weight, are saturated with $ClO_2$ gas. The gas reacts with the PVP causing the characteristic chlorine dioxide color to disappear. Certain other polymer types are disclosed which possess similar properties. The resulting product is an organically stabilized chlorine dioxide composition which is claimed to be a powerful microbicide, although no examples are provided to confirm this claim. The stabilized $ClO_2$ is postulated to exist in the reduced, trivalent chlorine, chlorite form, which is stabilized or complexed by the PVP. A related, chemically stabilized chlorite matrix is revealed by Kühne in U.S. Pat. Nos. 4,507,285 and 4,725,437, which matrices enclose activated oxygen for topical or systemic treatment of diseases and disorders.

In all of these teachings and disclosures there is no indication that free molecular $ClO_2$ can be held in solution per se, in the tetravalent chlorine form, for subsequent release by means other than acidification of the reduced chlorite form and partial chemical conversion to chlorine dioxide, i.e. from $[H^+]+[ClO_2^-] \rightarrow \rightarrow \rightarrow ClO_2, [Cl^-], [ClO_3^-]$. In many instances, however, the use of acids is counterindicated for certain applications. Specifically, a continued search has revealed that if significant levels of $ClO_2$ are required for, say, localized disinfection, wound treatment, or mouth odor oxidation, without the use of acid triggers of chlorite solutions, including so-called stabilized or complexed $ClO_2$ solutions, no compositions have yet been described which can meet this need. This invention was made as a result of that search.

OBJECTS AND SUMMARY OF THE INVENTION

Accordingly, it is a general object of the present invention to substantially alleviate the above-identified deficiencies of the prior art.

A specific object of the present invention is to provide a composition containing molecular chlorine dioxide, $ClO_2$, in a stable chelated form in aqueous solution, without reducing it to the chlorite form.

A further object of the present invention is to provide methods for release of the chlorine dioxide from the chelate avoiding the use of acids.

A further object of the present invention is to provide methods for use of chelated chlorine dioxide compositions for disinfection, wound treatment, oral and body cavity antisepsis and odor reduction, as well as other bleaching and oxidative actions where $ClO_2$ currently serves.

The present invention provides, in one aspect, a method for preparing stable compositions containing molecular chlorine dioxide in a chelated form, unlike previously-described stabilized chlorine dioxide compositions in which stability is achieved by conversion of the $ClO_2$ to the chlorite form. The chelates are comprised of the electron-deficient $ClO_2$ molecule, which can accept an electron, and a chelating agent which can contribute its available electrons to the accepting orbital of the $ClO_2$ molecule.

In another aspect, the present invention provides for selective release of $ClO_2$ from the otherwise stable chelated compositions by addition to their aqueous solutions of specific metal cations which displace the chlorine dioxide from the chelate to a degree dependent upon the relative strengths of the chelates of chlorine dioxide and the specific metal cation.

In another aspect of this invention, methods are provided for using the chelated chlorine dioxide compositions, with and without the addition of displacing metal cations, for the same purposes of disinfection, deodorization and bleaching for which unstabilized, molecular chlorine dioxide compositions are currently being employed.

In one embodiment, a chelated $ClO_2$ composition of this invention is used as a rinse to destroy oral malodorants and reduce the numbers of microorganisms which cause malodor, dental plaque and gum disease. In another embodiment, a $ClO_2$ chelate is used as a douche. In a further embodiment, a chelated $ClO_2$ composition is used as a surgical irrigant to provide disinfection and other beneficial effects imparted by the $ClO_2$ that is released upon contact with the ferric ion of blood hemoglobin in the cavity. In yet another embodiment, a zinc salt is added to a $ClO_2$ chelate composition which is then used to disinfect the eye or skin surfaces.

These and other aspects of this invention will become evident upon reference to the following detailed description.

DETAILED DESCRIPTION OF THE INVENTION

The present invention provides compositions and methods of use of chelated chlorine dioxide complexes, and their subsequent application for disinfection, deodorization, and oxidation as both chelated and thence-liberated free molecular $ClO_2$. The invention is based on the fact that the chlorine dioxide molecule exists virtually entirely as a permanent free radical monomer. The theoretical considerations which underlie this state are confirmed, in part, by the dipole moment and paramagnetic nature of the chlorine dioxide molecule. As a free radical, $ClO_2$ has an unpaired electron diffused in an outer orbital, and can readily accept or presumably share an electronic charge from an electron donor. One class of electron donors is the chelating agents, which have been classically characterized as compounds containing electron-donating atoms that can combine, by coordinate bonding, with single metal ions to form a cyclic structure called a chelation complex, or a chelate. The universal presence of metal ions in these chelates derives from the fact that metal ions, or certain metal ion radicals, are cations which are electron-deficient, and thus positively charged. I have now discovered that chlorine dioxide can function, in the same capacity, as do metal ions, by accepting electronic charges donated by chelating agents.

For descriptive purposes, the $ClO_2$ chelate formed with the specific chelating agent ethylenediamine tetraacetic acid, as the di-, tri- or tetrasodium salt shall be used to characterize the type of complex compositions that can be formed, and the methods of using such chelates. There are many related chelating agents which may also be used in place, wholly or in part, of this EDTA family. Each of these has somewhat different chemical and physical characteristics, including complex formation constants, qualities which those that are skilled in the art of chelation chemistry would have sufficient familiarity with to modify the $ClO_2$ chelate appropriate to the desired end need. Specific examples of chelating agents related to EDTA include hydroxyethylethylenediaminetriacetic acid, nitrilotriacetic acid, N-dihydroxyethylglycine and ethylenebis (hydroxyphenylglycine). Other classes of chelating agents, other than those in the aminocarboxylic acid category encompassing EDTA, would include but not be limited to 1,3-diketones, aminoalcohols, aromatic heterocyclic bases, oximes, and tetrapyrroles. Specific examples of 1,3-diketones are acetylacetone and thenoyltrifluoroacetone among others; of aminoalcohols are triethanolamine and N-hydroxyethylethylenediamine among others; of aromatic heterocyclic bases are dipyridyl and o-phenanthroline among others; of oximes are dimethylglyoxime and salicylaldoxime among others; and of tetrapyrroles are tetraphenylporphin and phthalocyanine among others. The characteristic of all of the structures in these classes is the presence of two or more donor atoms spatially situated so that they can coordinate with the same metal ion, or in this case, a chlorine dioxide. The chelate rings which form contain four or more members although five- or six-membered ring chelates are usually the most stable.

The chelate formed by EDTA can be represented by the following steric diagram, where $ClO_2$ would be contained in a central position that would be occupied by a metal ion in the corresponding metal chelate.

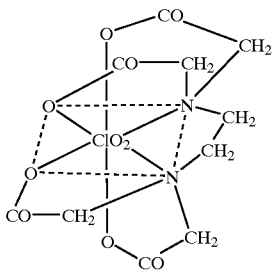

In order for EDTA to function as a chelating agent, at least two of its four carboxylic acid functions should exist in the ionized form, i.e. as $C(=O)-O^-$, so that its electrons are more freely available for donation. Thus chelates may be formed at a range of solution pH's at which $EDTA,Na_4$, $EDTA,Na_3$, and $EDTA,Na_2$ forms are stable. The practical lower pH limit of EDTA chelation with $ClO_2$ is about pH 2.0, which is consistent with the $pK_a$ values of the tetra-, tri-, di-, and mono-acid forms of EDTA of 2.00, 2.67, 6.16, and 10.26. Thus, at a pH of 2.67, where half of the EDTA present would be in the form of $EDTA,H_3,Na$ and half as $EDTA, H_2,Na_2$ (referred to earlier as $EDTA,Na_2$), only the latter form functions as a chelating agent, and less so as the pH is reduced. In fact, if a $ClO_2$-EDTA complex is prepared from a stoichiometric quantity of EDTA, at a pH where all of the agent was involved in chelation, the subsequent lowering of the solution pH would result in increasing liberation of chelated $ClO_2$ to the solution.

A more practical means of liberating $ClO_2$ from a chelate, without the addition of hydrogen ions $[H^+]$ and a resulting pH reduction, is by the introduction of those metal cations which have a greater affinity for the chelating agent than does the $ClO_2$. The equilibrium would shift to favor the chelate of the more strongly bound metal cation, resulting in the release of $ClO_2$ from the chelate. The greater the difference in the formation constants of the two chelates, metal and $ClO_2$, the greater the rapidity of displacement. It is also possible to displace $ClO_2$ from a chelate with a metal cation that forms a weaker complex, by taking advantage of the mass action principle of adding a large excess of the metal salt to a chelate solution. The molar ratio of metal cation added to displace $ClO_2$ from a chelate.$ClO_2$ complex to the total amount of chelate in solution is from about 0.1:1 to about 5:1, preferably about 0.5:1 to about 2:1, and most preferably about 1:1 to about 1.5:1.

This can be illustrated by the following study, where the level of $ClO_2$ displaced from an $EDTA.ClO_2$ complex [0.04 meq of $EDTA,Na_2$+23.5 ppm $ClO_2$] was spectrophotometrically determined at 370 nM five minutes after the addition of 0.2 ml of either a 1% or 2% metal salt solution or 0.5N HCl to 8 ml of the complex. The 1% or 2% concentration was chosen to adjust for the relative level of metal ion in the metal salt selected, in order to have a slight excess of metal ion in solution. The $ClO_2$ liberated is compared side-by-side with the logarithm of the formation constants of the corresponding EDTA-metal complex. The initial pH of 5 of the complex solution was minimally changed following the additions, except for the HCl addition, where the pH dropped to about 2.

| Metal/Cation | $ClO_2$ at 5 min. in ppm | log K |
|---|---|---|
| [$H_2O$ Control] | 0.5 | — |
| $Ba^{++}$(2%) | 0.3 | 7.8 |
| $Ca^{++}$(2%) | 0.2 | 10.7 |
| $Co^{++}$(2%) | 1.9 | 16.3 |
| $Zn^{++}$(1%) | 4.9 | 16.5 |
| $Cu^{+}$(1%) | 10.8 | 18.8 |
| $H^{+}$ | 16.5 | — |

While the measured concentrations below 1 ppm are considered imprecise, there is an apparent trend among these data which indicates that more strongly complexed metals show a greater displacement of $ClO_2$ from the chelate. This was further established in a subsequent study, using the $Fe^{+++}$ ion, which forms a stronger EDTA complex than any of the above ions: [log K for $Fe^{+++}$/EDTA complex=25.1]. In this study, the same 0.2 ml quantity of a 1% ferric chloride solution was added, several days later, to an aliquot of the same stable chelate solution. The treated solution rapidly developed a yellow-brown color, with an evident $ClO_2$ odor, and an absorbance at 370 nM corresponding to a $ClO_2$ level of 41.3 ppm. The reason for the apparently higher level of $ClO_2$ is unclear, but appears related to the unusual coloration, and increased absorbance at 370 nM, of the solution formed. The solution had a high microbiocidal activity, apparently superior to that of the original, unchelated $ClO_2$ solution, whereas the untreated EDTA.$ClO_2$ chelate had minimal activity. The color, and germ killing action may be related to the possible presence of the complex ion [$Cl_2O_4$]$^-$, the adduct of $ClO_2$ and $ClO_2^-$, which has been previously reported and which plays a role in certain $ClO_2$ oxidation reactions.

It was appropriate to consider one other possible source of $ClO_2$ production, resulting from the addition of $Fe^{+++}$ to the chelate solution, in order to properly validate the displacement of $ClO_2$ from the complex. Ferric ion has been reported to react with chlorite ion, where an electron transfer would result in ferrous ion and $ClO_2$ formation, i.e.:

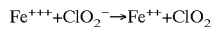

$$Fe^{+++} + ClO_2^- \rightarrow Fe^{++} + ClO_2$$

If excess chlorite existed in the $ClO_2$ solution to which the EDTA was added, this chlorite might possibly have reacted to form the $ClO_2$ observed, rather than it originating from displacement from the chelate. However when the same quantity of $Fe^{+++}$ solution was added to an activated chlorite solution from which the $ClO_2$ had been allowed to evaporate, leaving behind a residual amount of chlorite, no $ClO_2$ evolution nor yellow-brown color was noted as with the chelate. Thus the $ClO_2$ did indeed originate from metallic displacement from the chelate rather than simple oxidation of the chlorite.

This experiment also demonstrated that $ClO_2$, as the free molecule, is liberated from the chelate by metallic displacement, as opposed to that which is created by acidification and disproportionation of chlorite in so-called stabilized chlorine dioxide. The rapid evolution of $ClO_2$ from the complex, at a pH~5, could not occur with that rapidity by acidification of chlorite. In addition, even if a breakdown of chlorite would slowly occur at pH 5 to form $ClO_2$, the relative molar yield of the gas would have been much less, in favor of higher relative yields of chloride ion.

The range of $ClO_2$ concentrations which form chelate complexes covers the range from about 0 to at least 2500 ppm (0 to 38 meq/liter), and a preferred composition contains from about 1 ppm to about 1000 ppm (0.015 to 15 meq/liter). The level of chelating agent required to maintain stable $ClO_2$ chelates is generally proportionate to the level of $ClO_2$ in the solution, from about 0.1 to about 5 times the number of $ClO_2$ meq, preferably about 0.5 to about 3 times the number of $ClO_2$ meq, depending upon the nature of the chelate formed (e.g. mono-, di-, or tri-dentate). More preferably, this ratio is from about 0.5 to about 2 times, and most preferably from about 1.0 to about 1.5 times. The $ClO_2$ may be produced by any of the techniques known to those skilled in the art, whether by in situ oxidation or acidification of chlorite, reduction of chlorate, or external production of the gas by similar means and subsequent bubbling of the gas into water or the chelating solution. When the $ClO_2$ is produced in situ, the solution is then either adjusted to the desired final pH or the chelating material is introduced followed by pH adjustment. The pH range in which stable chelates may form, depending upon the chelating agent, is about 1.5 to about 13, with a preferred range of about 2 to about 12.

In order to preserve the stability of the $ClO_2$ in chelated form, a solution containing a chelate should contain cation and proton levels too low to substantially interfere with the formation and duration of a complex between the $ClO_2$ and the chelating agent. As used throughout the specification and claims, the phrase "absent sufficient metal cations and protons to substantially inhibit binding of the chlorine dioxide to the chelating agent" means that the metal cation and/or proton content of the solution does not substantially shift the equilibrium between the free $ClO_2$ in solution and the $ClO_2$ in solution which is in a complex with the chelating agent.

The $ClO_2$ chelates may be used for disinfection, wound treatment, deodorization, or other oxidative processes either per se or following activation. When used as such, reliance is placed on activation, and release of the $ClO_2$ by the substrate being contacted, be it surgical wound site, oral, ear canal or vaginal cavity, the skin or inanimate surface. In these situations, release may be effectuated by the presence on, or in the substrate of displacing metal ions, hydrogen ions or other materials which may disrupt the complex. Examples of triggering conditions would be the ferric ion from blood hemoglobin in a wound, calcium and magnesium in the bacterial membranes of gram (−) microorganisms, and the acidity created by lactic-producing bacteria in the vaginal vault. In contacting mucosal surfaces, such as within the vagina, there is a distinct advantage in using a $ClO_2$-containing complex, for acid triggered liberation of the germicide, rather than a so-called stabilized chlorine dioxide formulation based on chlorite, because the latter ion is known to be irritating and cytotoxic, whereas $ClO_2$ is better tolerated by the tissue.

Such chelating agents as EDTA have particular advantage in this invention, since they not only form stable complexes with $ClO_2$ but also have a well-recognized capacity to enhance the effectiveness of antimicrobials against gram (−) microorganisms. EDTA increases cell wall permeability by chelation of metal ions in their surface, so the chelate may serve a dual role of competitively abstracting metal ions from the microbial surfaces and replacing them, at the site, with liberated, microbiocidal $ClO_2$.

The present invention is illustrated by the following examples. Unless otherwise noted, all parts and percentages in the examples as well as the specifications and claims are by weight.

EXAMPLE 1

This example illustrates the preparation of a $ClO_2$ chelate, by the addition of the chelating agent $EDTA,Na_2$ to a solution of $ClO_2$ previously prepared by acidification of a sodium chlorite solution followed by neutralization of the excess acidity.

- 2 ml of a stock solution containing 15.0 mg/ml of chlorite ion was added to a flask, and the volume taken to 100 ml with deionized water.
- 8 ml of 0.5N HCl was added to the solution, the flask was covered and mixed, and the contents warmed in a microwave oven to about 50° C. The solution was held for 30 minutes while the yellow $ClO_2$ gas formed in solution.
- About 75 ml of cool deionized water was added to the flask, which was then shaken to dissolve the head space gas into the cool liquid. Then 4 ml of 1.0 N NaOH was added to the mixture, which was stirred, and the volume taken to 200 ml with deionized water.
- The absorbance of this solution at 370 nM was 0.499, corresponding to a $ClO_2$ concentration of 27.1 ppm.
- 6 ml of an $EDTA,Na_2$ solution containing 0.05 meq/ml was added to 150 ml of the $ClO_2$ solution, which decolorized within 1 minute after the mixture was shaken. The absorbance of the solution at 370 nM was now 0.008, corresponding to an unchelated $ClO_2$ concentration of 0.4 ppm. Based on the dilution factor, the total $ClO_2$ concentration of this solution would be 26.1 ppm, with 25.7 ppm existing in the chelate form and 0.4 ppm existing free.

EXAMPLE 2

This example illustrates the ability of the $EDTA.ClO_2$ complex, described in Example 1, to rapidly destroy the pathogenic microorganism *Escherichia coli*, following displacement of the $ClO_2$ by $Fe^{+++}$ in the chelate. The microbiocidal capability of three solutions were evaluated:

1) the unchelated $ClO_2$ solution, and 1→10 and 1→50 dilutions;
2) the chelated $ClO_2$ solution, and 1→10 and 1→50 dilutions;
3) the ferric iron-treated chelate of solution 2), where 0.75 ml of a 1% ferric chloride solution was added to 30 ml of solution 2) about 15 minutes before microbiological examination. Undiluted solution and 1→10 and 1→50 dilutions of this were evaluated.

0.1 ml of a challenge inoculum of the *E. coli* (ATCC No. 8739), suspended in saline, was introduced into 10 ml of the test solution, providing an organism concentration of 5.81 log cfu/ml. After 30 sec. or 2 min., 1 ml aliquots of each solution were transferred to Tryptone Azolectin Tween neutralizing broth, and plated out on Trypticase Soy Agar both directly and in serial $10^1$, $10^2$, and $10^3$ dilutions. The following log reductions were obtained for the three solutions at the two contact times:

| Time min | $ClO_2$ Control | | | $ClO_2$-Chelate | | | $ClO_2$-Chelate + $Fe^{+++}$ | | |
|---|---|---|---|---|---|---|---|---|---|
| | undil | 1:10 | 1:50 | undil | 1:10 | 1:50 | undil | 1:10 | 1:50 |
| | | | | log reduction of *E. coli* | | | | | |
| 0.5 | 3.21 | 3.11 | 3.51 | 0.07 | −0.01 | 0 | ≧3.81 | ≧3.81 | ≧3.81 |
| 2.0 | 3.41 | 3.33 | 3.51 | 0.03 | −0.05 | −0.02 | ≧3.81 | ≧3.81 | 2.86 |

These data demonstrate that, while the $ClO_2$ chelate has no rapid antimicrobial activity against the *E. coli* organism, once that chelated $ClO_2$ is displaced by ferric ion the resulting solution has an activity against that organism that is generally superior to that of the original $ClO_2$ solution. This is true even with the slight dilution of its concentration resulting from introduction of the activating iron solution. These data provide further confirmation that the $ClO_2$ has not undergone transformation to chlorite ion by introduction of the chelating agent, and then reconversion back to $ClO_2$ as a result of the iron displacement, since the reconversion is bound to be of less than 100% efficiency; while the data show equal or superior cidal efficacy equivalent to the original $ClO_2$ concentration.

EXAMPLE 3

This example illustrates the ability of an $EDTA.ClO_2$ complex, where the $ClO_2$ was prepared by direct oxidation of chlorite, to rapidly destroy the pathogenic microorganism *Staphylococcus aureus*, after displacement of the chelated $ClO_2$ by $Fe^{+++}$ ion. Specifically, the chlorine dioxide was prepared by fractional oxidation of 200 ml of a 1600 ppm sodium chlorite solution, at pH 6.4, by the addition of 5 ml of a 1260 ppm sodium hypochlorite solution. At the time of preparation, the solution contained 49.3 ppm of $ClO_2$, at which time 2 ml of a 0.05 meq/ml solution of $EDTA,Na_2$ was added to 150 ml of that solution, forming a colorless chelate solution. The unchelated $ClO_2$ in that solution was determined spectrophotometrically to be 1.5 ppm.

Two days after preparation of the chelate, its inherent cidal capacity was determined relative to that of the original $ClO_2$ solution, whose concentration had dropped to 41.2 ppm. This was accomplished through the addition of a 0.3 ml quantity of 1% ferric chloride to 12 ml of the chelate solution. The microbiocidal capability of the $ClO_2$ and the iron-triggered chelate solutions, and dilutions thereof, were evaluated as follows:

1) the unchelated $ClO_2$ solution, and 1→10 and 1→50 dilutions;
2) the ferric iron-treated chelate of solution 1), and 1→10 and 1→50 dilutions.

0.1 ml of a challenge inoculum of the *Staph. aureus* (ATCC No. 6538), suspended in saline, was introduced into 10 ml of the test solution, providing an organism concentration of 5.63 log cfu/ml. After 30 sec. or 2 min., 1 ml of each solution, and 10-fold dilutions thereof, were diluted with 100 ml of normal saline, after which the full volumes were passed through 0.45µ Millipore filters. The latter were placed on TSA plates, incubated for 48 hours at 35° C., and the total numbers of organisms per ml were determined. The following log reductions were obtained for the two solutions at the two contact times:

| Time min | $ClO_2$ Control | | | $ClO_2$-Chelate | | |
|---|---|---|---|---|---|---|
| | undil | 1:10 | 1:50 | undil | 1:10 | 1:50 |
| | log reduction of S. aureus | | | | | |
| 0.5 | 5.63 | 5.63 | 1.57 | 5.63 | 5.63 | 0.68 |
| 2.0 | 5.63 | 5.63 | 5.63 | 5.63 | 5.63 | 5.63 |

This example demonstrates that the $ClO_2$ released from the chelate is equally capable of destroying this gram (+) pathogen, even though some dilution of the original $ClO_2$ solution was sustained by dilution with both the EDTA chelating and the ferric chloride solutions. It also indicates that the chelate solution is capable of being stored.

EXAMPLE 4

This example demonstrates the ability of different metal ions to displace $ClO_2$ from a chelate depending upon the relative affinity of the chelating agent to $ClO_2$ and the metal ions. To each of three 5 ml portions of the chelated $ClO_2$ solution of Example 3 were added 1 drop of a 1:100 dilution of a commercial food dye preparation, which contained a mixture of FD&C Reds No. 40 and No. 3. To portion 1), the Control, two drops of water were added; to portion 2), two drops of a $Zn^{++}$ solution, providing about 0.15 meq of that ion; to portion 3), two drops of a $Fe^{+++}$ solution, providing about 0.12 meq of that ion. In solution 3), the pink coloration disappeared immediately; in solution 2), the pink color faded and disappeared over a several hour period; in solution 1), the pink color remained. This illustrates that the $Zn^{++}$ ion, which has a weaker formation constant with EDTA (log K=16.5) than with the $Fe^{+++}$ ion (log K=25.1), takes longer to competitively displace $ClO_2$ from its EDTA chelate than does ferric ion, so that the more rapidly displaced $ClO_2$ was able to bleach the pink coloration immediately, whereas the $ClO_2$ that was more slowly displaced by the zinc ion was only able to destroy the pink coloration at a slower rate.

EXAMPLE 5

This example illustrates the preparation of a highly concentrated solution of a $ClO_2$ chelate, useful, for example, as an oral rinse, a vaginal douche or an intramammary infusion to treat mastitis. 50 ml of a pH 7.15 solution containing 2255 ppm of chlorine dioxide (1.67 mM per 50 ml), were added to an Erlenmeyer flask containing 5 ml of a solution with 2.5 mM tetrasodium EDTA. Upon combination, the dark yellow color of the $ClO_2$ solution instantly disappeared, forming a colorless solution at pH 6.66. The UV Absorbance of that solution at 370 nM indicated a residual, unchelated, chlorine dioxide level of 13.8 ppm, which was 0.68% by weight of the total chlorine dioxide present.

When exposed to a strip of chlorine indicator paper, where the color change is based on the starch-iodine reaction, the color that formed corresponded to the highest color comparison strip. This indicated that the solution had an oxidizing power equivalent to a solution containing at least 200 ppm of chlorine, and by calculation at least 500 ppm of $ClO_2$. Since the reaction with the color strip took place at a near-neutral pH, the oxidizing power must have been derived from $ClO_2$, rather than a chlorite reduction product, since the latter ion, had it formed, will only oxidize the iodide in the indicator paper at acidic pHs, of about 3 and below.

The solution had an acceptable taste, and was found to be an efficient treatment for oral malodor.

It is clear that the present invention is well adapted to carry out the objects, and achieve the ends and advantages mentioned at the outset. While currently preferred embodiments of the invention have been described for purposes of this disclosure, numerous modifications may be made which will readily suggest themselves to those skilled in the art, and which are encompassed within the spirit of the invention disclosed, and as defined in the appended claims.

What is claimed is:

1. An aqueous composition consisting essentially of water and 1 to 2,500 ppm molecular chlorine dioxide in stable chelated form with a chelating agent, said chelating agent being present in said composition at a concentration of about 0.5 to about 5 times the concentration of chlorine dioxide, on a mole to mole basis, wherein (i) said aqueous composition is absent sufficient metal cations and protons to substantially inhibit binding of the chlorine dioxide to the chelating agent, and (ii) free, unchelated chlorine dioxide in said aqueous composition is no greater than 13.8 parts by million and not greater than about 3.04% by weight of total chlorine dioxide in the aqueous composition.

2. The composition of claim 1, wherein the chelated chlorine dioxide is reversibly bound to the chelating agent.

3. The composition of claim 1, wherein the chelating agent is selected from the group consisting of aminocarboxylic acids, 1,3-diketones, aminoalcohols, aromatic heterocyclic bases, oximes and tetrapyrroles.

4. The composition of claim 3, wherein the chelating agent is ethylenediamine tetraacetic acid as its di-, tri- or tetrametal salt.

5. The composition of claim 1, wherein the concentration of chlorine dioxide in the solution is from about 1 to about 1000 ppm.

6. The composition of claim 1, wherein the molar ratio of chelating agent to chlorine dioxide is from about 0.5 to about 3.

7. The composition of claim 1, wherein the aqueous solution has a pH from about 1.5 to about 13.

8. The composition of claim 7, wherein the pH is from 2 to 12.

* * * * *